United States Patent

(12)
Lorant

(10) Patent No.: US 6,509,024 B2
(45) Date of Patent: Jan. 21, 2003

(54) COMPOSITION IN THE FORM OF WATER-IN-OIL EMULSION AND ITS COSMETIC USES

(75) Inventor: Raluca Lorant, Thiais (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/813,032

(22) Filed: Mar. 21, 2001

(65) Prior Publication Data

US 2001/0041768 A1 Nov. 15, 2001

(30) Foreign Application Priority Data

Mar. 21, 2000 (FR) .............................. 00 03589

(51) Int. Cl.$^7$ ................................ A61K 7/02
(52) U.S. Cl. ................ 424/401; 424/70.12; 424/78.02; 424/78.35; 516/23; 516/27; 514/837; 514/846
(58) Field of Search .............................. 424/401, 70.12, 424/78.02, 78.35; 516/23, 27; 514/846, 837

(56) References Cited

U.S. PATENT DOCUMENTS

| 5,262,087 A | 11/1993 | Tachibana et al. |
| 5,412,004 A | 5/1995 | Tachibana et al. |
| 5,470,551 A | 11/1995 | Dubief et al. |
| 5,811,487 A | 9/1998 | Schulz et al. ................ 524/862 |
| 6,346,256 B1 * | 2/2002 | Simon ........................ 424/401 |

OTHER PUBLICATIONS

11092335, Jun. 4, 1999, Patent Abstracts of Japan.
11021227, Jan. 26, 1999, Patent Abstracts of Japan.

* cited by examiner

*Primary Examiner*—Margaret G. Moore
(74) *Attorney, Agent, or Firm*—Oblon, Spivak, McClelland, Maier & Neustadt, P.C.

(57) ABSTRACT

The first embodiment of the present invention provides a composition, which includes:
 an aqueous phase dispersed in an oily phase;
 wherein the oily phase includes at least one particle of a crosslinked solid organopolysiloxane elastomer having at least one oxyalkylene group,
 and wherein the aqueous phase includes at least one crosslinked and at least partially neutralized poly(2-acrylamido-2-methylpropanesulphonic acid) polymer. Other embodiments of the present invention provide methods of using the above-identified composition, compositions containing same, and a method of preparing water-in-oil emulsions.

34 Claims, No Drawings

COMPOSITION IN THE FORM OF WATER-IN-OIL EMULSION AND ITS COSMETIC USES

BACKGROUND OF THE INVENTION

1. Field of the Invention

The invention relates to a water-in-oil (W/O) emulsion which contains an oxyalkylenated crosslinked organopolysiloxane elastomer and a specific polymer and to its uses. The present invention is particularly suitable in the cosmetic and/or dermatological fields, in products for caring for, cleansing and/or making up the skin.

2. Discussion of the Background

It is commonplace in the cosmetic or dermatological fields to use compositions which have the appearance of a cream and which are composed of a water-in-oil (W/O) emulsion wherein an aqueous phase is dispersed in an oily phase. In the fields under consideration, a cream is a composition which exhibits a degree of viscosity different from liquid or semi-liquid compositions, such as lotions and milks, or from solid compositions.

W/O emulsions include a continuous oily phase and thus make it possible to form, on the surface of the skin, a lipid film which prevents transepidermal water loss and protects the skin from external attacks. These emulsions are particularly appropriate for protecting and nourishing the skin and in particular for treating dry skin.

Creams in the form of W/O emulsions exhibit the disadvantage of being uncomfortable because of the greasy, heavy and sometimes even sticky feeling contributed by this external fatty phase which remains on the skin. Thus, these creams are generally used for dry skin, being too greasy to be used on greasy skin. Furthermore, they do not contribute freshness and are generally too rich in oil to be used during the summer or in hot countries.

To overcome these disadvantages, W/O emulsions with a high water content have been envisaged. The water content cannot be too high, however, for reasons of stability or because the high water content must be offset by the addition of several surfactants (which can undesirably reduce the comfort feeling of the final composition and can even result in skin irritation problems, in particular in subjects with sensitive skin) and/or by the addition of electrolytes (which have the disadvantage of being incompatible with a large number of ingredients and active principles which are used in cosmetic and dermatological compositions).

The need thus remains for a composition in the form of a water-in-oil emulsion which can be used in the cosmetic and/or dermatological fields and which does not exhibit the above-mentioned disadvantages, in particular which provides freshness without contributing a greasy or sticky effect when applied to the skin, while having good stability. The term "emulsion of good stability" is understood to mean in this instance an emulsion which is homogeneous and even and which does not exhibit phase separation (separation of the aqueous phase and the oily phase) or release of oil, at least for two months at 45° C.

SUMMARY OF THE INVENTION

One object of the present invention is to provide a water-in-oil emulsion which can be used in the cosmetic and/or dermatological fields and which does not exhibit the disadvantages of conventional compositions.

Another object of the present invention is to provide a water-in-oil emulsion which provides freshness without contributing a greasy or sticky effect when applied to the skin.

Another object of the present invention is to provide a water-in-oil emulsion having good stability.

Another object of the present invention is to provide a water-in-oil emulsion which is homogeneous.

Another object of the present invention is to provide a water-in-oil emulsion which does not exhibit phase separation (separation of the aqueous phase and the oily phase) or release of oil, at least for two months at 45° C.

Another object of the present invention is to provide a water-in-oil emulsion which can contain a large amount of water while being very stable.

These objects, and others, may be accomplished with the present invention, the first embodiment of which provides a composition, which includes:

an aqueous phase dispersed in an oily phase;
wherein the oily phase includes at least one particle of a crosslinked solid organopolysiloxane elastomer having at least one oxyalkylene group,
and wherein the aqueous phase includes at least one crosslinked and at least partially neutralized poly(2-acrylamido-2-methylpropanesulphonic acid) polymer.

Another embodiment of the present invention provides a method of using the above-identified composition, which method includes applying the composition to at least one selected from the group including hair, scalp, skin, lips, nails, mucous membranes and combinations thereof.

Another embodiment of the present invention provides a method of treating greasy skin, hair, lips or scalp, which method includes applying the above-identified composition to at least one selected from the group including skin, hair, lips, scalp and combinations thereof.

Another embodiment of the present invention provides a cosmetic or dermatological composition, which includes the above-identified composition and a pharmaceutically acceptable medium.

Another embodiment of the present invention provides a method for stabilizing a water-in-oil emulsion that includes an aqueous phase dispersed in an oily phase, the method includes:

contacting the oily phase with at least one particle of a crosslinked solid organopolysiloxane elastomer having at least one oxyalkylene group; and
contacting the aqueous phase with at least one crosslinked and at least partially neutralized poly(2-acrylamido-2-methylpropanesulphonic acid) polymer,
to stabilize the water-in-oil emulsion.

Another embodiment of the present invention provides a method of preparing a water-in-oil emulsion, which includes:

dispersing an aqueous phase in an oily phase; wherein
the oily phase includes at least one particle of a crosslinked solid organopolysiloxane elastomer having at least one oxyalkylene group; and
the aqueous phase includes at least one crosslinked and at least partially neutralized poly(2-acrylamido-2-methylpropanesulphonic acid) polymer.

The composition according to the invention has the advantage of being very stable, even in the absence of electrolyte and/or even in the presence of a large amount of aqueous phase.

DESCRIPTION OF THE PREFERRED EMBODIMENTS

Various other objects, features and attendant advantages of the present invention will be more fully appreciated as the same becomes better understood from the following detailed description of the preferred embodiments of the invention.

The present inventors have found that it is possible to obtain a water-in-oil emulsion composition, which can contain a large amount of water but which is very stable, which includes a combination of an oxyalkylenated crosslinked organopolysiloxane elastomer and of a crosslinked and at least partially neutralized poly(2-acrylamido-2-methylpropanesulphonic acid) polymer.

A preferred embodiment of the invention is a composition that includes, in a physiologically acceptable medium, an aqueous phase dispersed in an oily phase, characterized in that the oily phase includes particles of a crosslinked solid organopolysiloxane elastomer having at least one oxyalkylene group and in that the aqueous phase includes at least one crosslinked and neutralized poly(2-acrylamido-2-methylpropanesulphonic acid) polymer.

The term "physiologically acceptable medium" is understood to mean, in the present invention, a nontoxic medium compatible with the skin (including the inside of the eyelids), mucous membranes, hair or lips of human beings.

The composition of the invention has the advantage of being homogeneous and of remaining stable over time, even when it contains a large amount of internal aqueous phase. In addition, it has the advantage of not requiring the addition of electrolytes generally used to stabilize W/O emulsions. It can thus advantageously be devoid of electrolytes. More preferably, it is devoid of electrolytes such as $MgSO_4$.

Thus, another preferred embodiment is the use of the combination of particles of a crosslinked solid organopolysiloxane elastomer having at least one oxyalkylene group and of at least one crosslinked and neutralized poly(2-acrylamido-2-methylpropanesulphonic acid) polymer for obtaining a stable water-in-oil emulsion.

Another preferred embodiment is the use of the combination of particles of a crosslinked solid organopolysiloxane elastomer having at least one oxyalkylene group and of at least one crosslinked and neutralized poly(2-acrylamido-2-methylpropanesulphonic acid) polymer as agent for stabilizing a water-in-oil emulsion.

Furthermore, the composition of the invention has the advantage of being very fresh and non-sticky when applied to the skin while having a very comfortable feel (softness, absence of irritation).

The crosslinked solid organopolysiloxane elastomer having at least one oxyalkylene group used in the composition of the invention makes it possible at least in part to ensure the dispersion of the aqueous phase in the oily phase of the emulsion.

The term "solid elastomer" is understood to mean a flexible and deformable material having viscoelastic properties and in particular the consistency of a sponge or of a flexible sphere. Its modulus of elasticity is such that this material is resistant to deformation and has a limited ability to expand and to contract. This material is capable of returning to its original shape after it has been stretched. This elastomer is preferably formed of polymeric chains of high molecular weight, the mobility of which is limited by a uniform network of crosslinking points.

The organopolysiloxanes of the composition of the invention includes one or more oxyalkylene groups, and preferably one or more oxyethylene (OE) groups, more preferably from 1 to 40 oxyalkylene units, more particularly preferably from 10 to 30, better still from 10 to 20, more especially preferably from 12 to 20 and even better still from 12 to 18 oxyalkylene units, which can form polyoxyalkylene and more preferably polyoxyethylene chains. These ranges include all values and subranges therebetween, including 2, 4, 6, 8, 14, 16, 24, 28, 32 and 38 oxyalkylene groups. These groups can be pendant, at the chain end or connecting two parts of the silicone structure. The silicon atoms carrying these groups preferably number from approximately 1 to 10, more preferably from 2 to 8 and better still from 3 to 6, which ranges include all values and subranges therebetween, including 4, 5, 7 and 9.

Although the invention preferably includes organopolysiloxanes having oxyethylene groups(s) (namely, having only oxyethylene groups as the oxyalkylene groups), it can also include organopolysiloxanes having oxypropylene group(s), that is to say only having oxypropylene groups as the oxyalkylene groups. The organopolysiloxanes can also include both one or more oxyethylene (OE) group(s), for example 1 to 20, more preferably 10 to 20, more especially preferably 12 to 20 and even better still from 12 to 18 oxyethylene units, and one or more oxypropylene (OP) group(s), for example 0 to 20, more preferably 1 to 20, more especially preferably 10 to 20, more particularly preferably 12 to 20 and even better still from 12 to 18 oxypropylene units; these organopolysiloxanes are also known as organopolysiloxanes having alkylethoxy-propylene group(s). Each of these aforementioned OE and OP ranges include all values and subranges therebetween, including 2, 4, 6, 8, 14 and 16 oxyalkylene groups. These groups can be pendant, at the chain end or connecting two parts of the silicone structure. The silicon atoms carrying these respective groups preferably number from approximately 1 to 10, more preferably from 2 to 8 and better still from 3 to 6, which ranges include all values and subranges therebetween, including 4, 5, 7 and 9. The number of oxyethylene groups is most preferably greater than the number of oxypropylene groups.

The silicone structure forming the polymeric backbone of the organopolysiloxane that contains the oxyalkylene group (s) is advantageously a polydimethylsiloxane (PDMS) structure, a portion of the methyl groups of which is optionally substituted by one or more $C_2$ to $C_{30}$ and preferably $C_8$ to $C_{24}$ and better still from $C_{10}$ to $C_{20}$ alkyl groups or phenyl groups, either at the chain end or at pendant positions. These ranges include all values and subranges therebetween, including those having 3, 4, 5, 6, 7, 9, 11, 12, 13, 14, 15, 16, 17, 18, 19, 21, 22, 23, 25, 26, 27, 28 and 29 carbons. Mixtures of substituents are possible along the PDMS chain.

The organopolysiloxane having the oxyalkylene group(s) can include one or more silicone backbone(s) connected to one another by one or more oxyalkylene and preferably oxyethylene groups as defined above or by one or more alkylene groups, the alkylene group number ranging from 1 to 30 and preferably from 10 to 20, which ranges include all values and subranges therebetween, including those having 2, 3, 4, 5, 6, 7, 8, 9, 11, 12, 13, 14, 15, 16, 17, 18, 19, 21, 22, 23, 24, 25, 26, 27, 28 and 29 carbons. Mixtures of alkylene groups are possible. It preferably includes at least two polymeric backbones connected to one another. The silicone backbone or backbones of the organopolysiloxanes of the composition according to the invention preferably includes from 26 to 80 silicon atoms. More preferably, the silicon backbone or backbones of the organopolysiloxanes includes from 32 to 60 silicon atoms, more particularly preferably from 40 to 50 silicon atoms, which ranges include all values and subranges therebetween, including 30, 38, 44, 54, 62, 68, 74, and 78 silicon atoms.

The organopolysiloxane elastomers used in the composition in accordance with the invention are partially or completely crosslinked and have a three-dimensional structure. When present in an oily phase, they are preferably converted, according to the level of oily phase used, from a product with a spongy appearance, when they are used in the presence of small contents of oily phase, to a homogeneous gel, in the presence of larger amounts of oily phase. The gelling of the oily phase by these elastomers can be complete or partial. Preferably, the degree of crosslinking is at least 25%, more preferably at least 50%, more particularly preferably at least 75%, and most preferably about 100%, which ranges include all values and subranges therebetween, including 30, 40, 45, 60, 70, 80, 85, and 90%. The degree of crosslinking is easily determined according to known methods in the polymer art.

These organopolysiloxane elastomers can be provided in the form of a powder, the particles constituting this powder having a size generally ranging from 0.1 to 500 μm, preferably from 3 to 200 μm and better still from 10 to 50 μm and being able to be spherical, flat or amorphous with, preferably, a spherical shape. These ranges include all values and subranges therebetween, including 0.5, 1, 5, 15, 25, 75, 100, 150, 250, 300 and 400 μm They can also be provided in the form of an anhydrous gel comprising the organopolysiloxane elastomer dispersed in an oily phase. This oily phase, also known as liquid fatty phase, can include any non-aqueous substance or mixture of non-aqueous substances which is liquid at room temperature (approximately 25° C.) and at atmospheric pressure (760 mm of Hg).

The organopolysiloxane elastomers used according to the invention are preferably chosen from the crosslinked polymers obtained by an addition and crosslinking reaction in a non-aqueous medium, in the presence of a catalyst, in particular of the platinum type, of at least:

(a) one first organopolysiloxane (i) having at least two vinyl groups in the α,Ω-position of the silicone chain; and (b) one second organopolysiloxane (ii) having at least one hydrogen atom bonded to a silicon atom per molecule and at least one oxyalkylene, in particular oxyethylene, group.

The organopolysiloxane (i) is preferably chosen from polydimethylsiloxanes (PDMSs) and is more especially an α,Ω-dimethylvinylpolydimethylsiloxane. The organopolysiloxane (ii) is preferably chosen from polydimethylsiloxanes having one or more hydrogen atom(s), each bonded to a silicon atom, and one or more oxyethylene groups and optionally one or more oxypropylene groups bonded to a silicon atom via an alkylene radical having from 1 to 22 carbon atoms. More preferably, the alkylene radical has from 2 to 20 carbon atoms, more particularly preferably from 4 to 18 carbon atoms, and most preferably 6 to 16 carbon atoms, which ranges include all values and subranges therebetween, including 3, 5, 7, 9, 10, 11, 12, 13, 14, 15, 17, 19 and 21 carbon atoms.

The silicone chains of the first and second organopolysiloxanes (i) and (ii) optionally have $C_1$ to $C_6$ alkyl pendant chains and/or aryl chains. The range given for the alkyl pendant chains includes all values and subranges therebetween, including 2, 3, 4, and 5 carbons.

As indicated above, the organopolysiloxane elastomers which can be used in the composition according to the invention are advantageously provided in an oily phase, with which they preferably constitute an anhydrous gel. This gel is preferably obtained as follows:

(a) mixing the first organopolysiloxane (i) and the second organopolysiloxane (ii);

(b) adding an oily phase to the mixture of stage (a); and (c) polymerizing the first organopolysiloxane (i) and the second organopolysiloxane (ii) in the oily phase in the presence of a platinum catalyst.

The oily phase used during the manufacture of the anhydrous gel may include one or more oils which are liquid at room temperature (approximately 25° C.) chosen from hydrocarbonaceous oils and/or silicone oils. The oily phase is more preferably a silicone liquid phase including one or more oils chosen from polydimethylsiloxanes (PDMSs) with a linear or cyclic chain which are liquid at room temperature, optionally including a pendant alkyl or aryl chain or an alkyl or aryl chain at the chain end, the alkyl chain having from 1 to 6 carbon atoms. The alkyl chain range includes all values and subranges therebetween, including 2, 3, 4, and 5 carbon atoms.

The organopolysiloxanes of the invention are preferably obtained according to the procedure of Examples 3, 4 and 8 of U.S. Pat. No. 5,412,004 and of the examples of U.S. Pat. No. 5,811,487, the entire contents of each of which being hereby incorporated by reference.

Preferably the organopolysiloxanes of the composition of the invention are, for example, that sold under the reference KSG 21 by Shin Etsu or the product of Example 3 (synthetic example) of U.S. Pat. No. 5,412,004.

KSG 21 is provided in the form of a pasty gel that includes approximately 28% of crosslinked organopolysiloxane comprising oxyethylene group(s) and 72% of silicone oil (PDMS) having a viscosity of 6 cSt (i.e., $6\times10^{-6}$ m$^2$/s). The percentages are given by weight, based on the total weight of the gel.

The product of Example 3 (synthetic example) of U.S. Pat. No. 5,412,004 is provided in the form of a pasty gel that includes approximately 33% by weight of crosslinked organopolysiloxane that contains oxyethylene group(s) and approximately 67% by weight of 6 cSt PDMS (i.e., $6\times10^{-6}$ m$^2$/s). The organopolysiloxane contains approximately 18% of ethylene oxide by weight with respect to the total weight of the polymer.

The elastomer gel of the invention preferably has a plastic rheological behaviour exhibiting a viscosity at low shear in the region of $10^{-3}$ s$^{-1}$ or $10^{-4}$ s$^{-1}$, ranging from $2\times10^6$ poises to $4\times10^6$ poises ($2\times10^5$ Pa·s to $4\times10^5$ Pa·s) and a dynamic viscosity of 15 to 50 poises (1.5 to 5 Pa·s) for a shear rate of 200 s$^{-1}$ at $t_{10\ minutes}$, measured with an RS 75 (Haake) controlled-stress rheometer at 25° C. in cone/plate geometry; characteristics of the cone: diameter of 20 mm, angle of 1° and gap of 40 μm. Preferably, this organopolysiloxane additionally has a viscoelastic behaviour with a dominant elastic nature at low values of the shear stress defined as follows: 800 Pa<G* plate<2,500 Pa with $\delta_{plate}$ in the region of 10°, G*$_{plate}$ representing the consistency and $\delta_{plate}$ representing the elasticity, this measurement being made at 1 Hz. It preferably exhibits a flash point of approximately 170° C. at atmospheric pressure.

For the product of Example 3 (synthetic example) of U.S. Pat. No. 5,412,004, the dynamic viscosity, under the conditions indicated above, is 45 poises (4.5 Pa·s).

The organopolysiloxane elastomer gel is preferably present in the composition of the invention in an amount ranging from 0.3 to 30% by weight and better still from 1.5 to 18% by weight with respect to the total weight of the composition (which ranges include all values and subranges therebetween, including 0.5, 0.8, 1, 2, 4, 6, 8, 10, 16, 20, 24 and 26% by weight), which corresponds to a level of organopolysiloxane elastomer, as active material, preferably ranging from 0.1 to 10% by weight and better still from 0.5 to 6% by weight with respect to the total weight of the composition (which ranges include all values and subranges therebetween, including 0.2, 0.8, 1, 2, 3, 4 and 5% by weight).

The organopolysiloxane elastomer of the invention is in particular a surfactant with an HLB (Hydrophilic Lipophilic Balance) of approximately 2.5.

The oily phase of the composition according to the invention can include, in addition to the oil possibly present in the anhydrous gel as a mixture with the crosslinked organopolysiloxane elastomer, any kind of oil and fatty substance known to a person skilled in the art to which this invention pertains, such as, for example, oils of vegetable origin (jojoba, avocado, sesame, sunflower, maize, soybean, safflower or grape seed), mineral oils (liquid petrolatum or isoparaffins), synthetic oils (isopropyl myristate, cetearyl octanoate, polyisobutylene, ethylhexyl palmitate or alkyl benzoates), volatile and non-volatile silicone oils, such as polydimethylsiloxanes and cyclic silicones (cyclodimethylsiloxanes or cyclomethicones), fluorinated or fluorosilicone oils, and mixtures of these oils.

The oily phase of the composition of the invention preferably includes at least one volatile oil in an amount of at least 1% by weight and preferably ranging from 2 to 35% by weight and better still from 5 to 25% by weight with respect to the total weight of the composition. These ranges include all values and subranges therebetween, including 3, 4, 6, 8, 10, 15, 17, 20, 22, 27, 28, 30 and 32% by weight. The term "volatile oil" is understood to mean an oil capable of evaporating, in less than one hour, on contact with the skin or lips which has in particular a non-zero vapour pressure ranging especially from $10^{-3}$ to 300 mm of Hg (at room temperature and atmospheric pressure) and preferably of greater than 0.3 mm of Hg. The volatile oil can be preferably chosen from hydrocarbonaceous oils (that is to say, having only carbons and hydrogens) with a branched chain, such as isohexadecane and isododecane, and from volatile silicone oils (that is to say, silicone oils having a viscosity of less than 8 cSt), such as, for example, cyclic silicones (cyclomethicones), such as cyclopentamethicone, cyclotetramethicone or cyclohexamethicone, and their mixtures.

The oily phase can additionally include other fatty constituents, such as fatty alcohols, for example stearyl alcohol, cetyl alcohol and cetearyl alcohol, and fatty acids. Mixtures are possible.

When the composition is used as a make-up-removing composition, in particular for removing makeup from the skin and/or eyes, it can advantageously include a make-up-removing oil. The make-up-removing oil can be preferably chosen from fatty acid esters having at least 12 carbon atoms and more preferably those obtained from an alcohol with a straight or branched chain having from 1 to 17 carbon atoms and from a fatty acid with a straight or branched chain having at least 12 carbon atoms and preferably from 14 to 22 carbon atoms. These respective ranges include all values and subranges therebetween, including 2, 3, 4, 5, 6, 7, 8, 9, 10, 11, 13, 15, 16, 18, 19, 20 and 21 carbon atoms as appropriate. They are preferably mono- or diesters. These esters preferably do not contain any unsaturation and/or any ether or hydroxyl group. Most preferably, it is a saturated ester which does not include any ether or hydroxyl group.

Preferable fatty acid esters which can be used as make-up-removing oil include 2-ethylhexyl palmitate (or octyl palmitate), 2-ethylhexyl myristate (or octyl myristate), isopropyl palmitate, isopropyl myristate, diisopropyl adipate, 2-ethylhexyl hexanoate, ethyl laurate, methyl myristate, octyldodecyl octanoate, isodecyl neopentanoate, ethyl myristate, myristyl propionate, 2-ethylhexyl 2-ethylhexanoate, 2-ethylhexyl octanoate, 2-ethylhexyl caprate/caprylate, methyl palmitate, butyl myristate, isobutyl myristate, ethyl palmitate, isohexyl laurate, hexyl laurate, isopropyl isostearate and their mixtures.

The oily phase is present in the composition according to the invention in an amount ranging from 5 to 50% and preferably from 10 to 25% by weight with respect to the total weight of the composition. These ranges include all values and subranges therebetween, including 6, 7, 8, 9, 12, 15, 18, 20, 27, 35, 40, 45 and 48% by weight.

The poly(2-acrylamido-2-methylpropane-sulphonic acid) polymers which can be used in the composition of the invention are crosslinked and neutralized. The term "neutralized" is understood to mean, in the present invention, completely or virtually completely charge neutralized polymers, that is to say at least 90% neutralized. These polymers are soluble or swellable in water. They are generally characterized in that they include, distributed randomly:

a) from 90 to 99.9% by weight of units of following general formula (I):

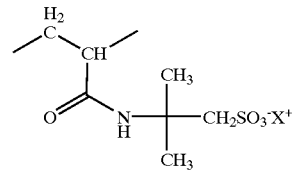

(I)

in which $X^+$ denotes a cation or a mixture of cations, it being possible for at most 10 mol % of the $X^+$ cations to be $H^+$ protons;

b) from 0.01 to 10% by weight of crosslinking units originating from at least one crosslinking monomer having at least two olefinic double bonds; the proportions by weight being defined with respect to the total weight of the polymer.

The polymers of the invention preferably include a number of units of formula (I) in an amount sufficiently high to produce polymer particles with a hydrodynamic volume in solution in water exhibiting a radius ranging from 10 to 500 nm and with a homogeneous and unimodal distribution.

The poly(2-acrylamido-2-methylpropane-sulphonic acid) polymers above includes 90 to 99.9% by weight of units of formula (I). More preferred polymers according to the invention include from 98 to 99.5% by weight of units of formula (I) and from 0.2 to 2% by weight of crosslinking units (b). The ranges given for the polymers includes all values and subranges therebetween, including 91, 92, 93, 94, 95, 96, 97, 99, 99.1, 99.3, and 99.7%.

In the formula (I), $X^+$ represents a cation or a mixture of cations preferably chosen from a proton, an alkali metal cation, a cation equivalent to that of an alkaline earth metal or the ammonium ion. Mixtures of different $X^+$ counterions are possible.

Preferably, 90 to 100 mol % of the cations are $NH_4^+$ cations and 0 to 10 mol % are protons ($H^+$). The non-protonic cation range include all values and subranges therebetween, including 91, 92, 93, 94, 95, 96, 97, 98 and 99 mol %.

The crosslinking monomers having at least two olefinic double bonds are preferably chosen, for example, from dipropylene glycol diallyl ether, polyglycol diallyl ethers, triethylene glycol divinyl ether, hydroquinone diallyl ether, tetraallyloxyethane or other allyl or vinyl ethers of polyfunctional alcohols, tetraethylene glycol diacrylate, triallylamine, trimethylolpropane diallyl ether, maethylenebisacrylamide or divinylbenzene. Mixtures are possible.

The crosslinking monomers having at least two olefinic double bonds are more preferably chosen from those corresponding to the following general formula (II):

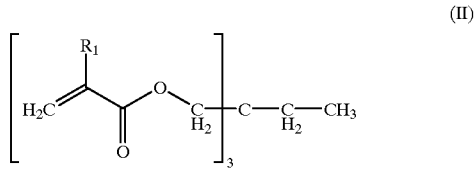

(II)

in which $R_1$ denotes a hydrogen atom or a $C_1$–$C_4$ alkyl and more preferably ethyl or propyl, and more particularly preferably methyl. Most preferably, the crosslinking monomer is trimethylolpropane triacrylate (compound of formula II where $R_1$ is hydrogen).

The particularly preferred polymers are those exhibiting a viscosity, measured with a Brookfield viscometer, rotor 4, at a rotational speed of 100 revolutions/minute in a 2% aqueous solution at a temperature of approximately 25° C., of greater than or equal to 1,000 cPs (or 1,000 mPa·s) and more preferably ranging from 5,000 to 40,000 cPs (5,000 to 40,000 mPa·s) and more particularly from 6,500 to 35,000 cPs (6,500 to 35,000 mPa·s). These ranges include all values and subranges therebetween, including 1,500, 2,500, 4,000, 7,500, 9,500, 10,000, 20,000, 30,000, and 38,000 cPs.

Preferably, the crosslinked and neutralized poly(2-acrylamido-2-methylpropanesulphonic acid)s used in the composition of the invention is obtained according to the preparation process having at least the following stages:

(a) the 2-acrylamido-2-methylpropanesulphonic acid monomer is dispersed or dissolved in the free form in a tert-butanol or water and tert-butanol solution;

(b) the solution or the dispersion of monomer obtained in (a) is neutralized with one or a number of inorganic or organic bases, preferably ammonia $NH_3$, in an amount which makes it possible to obtain a degree of neutralization of the sulphonic acid functional groups of the polymer ranging from 90 to 100%;

(c) the crosslinking monomer or monomers is/are added to the solution or dispersion obtained in (b);

(d) a conventional radical polymerization is carried out in the presence of free radical initiators at a temperature ranging from 10 to 150° C., the polymer precipitating in the solution or dispersion based on tert-butanol.

The poly(2-acrylamido-2-methylpropanesulphonic acid) used in the composition of the invention is preferably the product sold by the company Hoechst under the trade name "Hostacerin AMPS" (CTFA name: ammonium polyacryldimethyltauramide).

The crosslinked and neutralized poly(2-acrylamido-2-methylpropanesulphonic acid) used in the composition of the invention is preferably present in an amount ranging from 0.1 to 10% by weight of active material, better still from 0.2 to 5% by weight and more preferably from 0.5 to 3% by weight with respect to the total weight of the composition.

These ranges include all values and subranges therebetween, including 0.3, 0.7, 1, 2, 3, 4, 5, 6, 7, 8 and 9% by weight of active material.

According to a preferred embodiment of the invention, the composition according to the invention contains at least 65% by weight of aqueous phase with respect to the total weight of the composition and preferably at least 75% with respect to the total weight of the composition for the purpose of introducing maximum freshness. Preferably, the aqueous phase can constitute up to 90% of the total weight of the composition.

According to a more preferred embodiment of the invention, the water of aqueous phase constitutes at least 40% and preferably at least 50% of the total weight of the composition. These ranges include all values and subranges therebetween, including 42, 45, 48, 52, 55, 60, 62, 70, 72, 78, 82, 85, and 89% of the total weight of the composition.

The composition according to the invention preferably constitutes a cosmetic composition. The term "cosmetic composition" is understood to mean a product which has a pleasant appearance, a pleasant smell and a pleasant feel and which is intended for a topical application. This composition may be applied in a large number of treatments, in particular cosmetic treatments, of the skin, including the scalp, the hair, the nails and/or the mucous membranes, in particular for caring for, cleansing and/or making up and/or for the anti-sun protection of the skin and/or the mucous membranes, and for the preparation of a cream intended for the treatment of the skin, more particularly of greasy skin (contribution of freshness).

Thus, a preferred embodiment of the present invention is the cosmetic use of the composition as defined above in treating, protecting, caring for, removing make-up from and/or cleansing the skin, lips and/or hair and/or in making up the skin and/or the lips.

Another preferred embodiment of the present invention is a process for the cosmetic treatment of the skin, including the scalp, the hair and/or the lips, characterized in that a composition as defined above is applied to the skin, the hair and/or the lips.

Another preferred embodiment of the invention is the use of the composition as defined above in the manufacture of a cream intended for the treatment of greasy skin.

In a known way, the composition of the invention may optionally contain adjuvants usual in the cosmetic and/or dermatological fields, such as active principles, preservatives, antioxidants, complexing agents, solvents, fragrances, fillers, bactericides, odour absorbers, colouring materials (dyes and pigments) and lipid vesicles. Mixtures are possible. The amounts of these various adjuvants are those conventionally used in the field under consideration, for example from 0.01 to 20% by weight of the total weight of the composition, which range includes all values and subranges therebetween, including 0.05, 0.1, 1, 2, 4, 6, 8, 10, 12, 16 and 18% by weight. These adjuvants, depending upon their nature, can be introduced into the fatty phase, into the aqueous phase and/or into the lipid vesicles.

Preferable hydrophilic solvents include, for example, lower alcohols having 2 to 8 carbon atoms, such as ethanol and isopropanol, and polyols, such as glycerol and glycols.

Preferable fillers which can be used in the composition of the invention include, for example, powders derived from natural organic materials, such as maize, wheat or rice starches, which may or may not be crosslinked, in particular powders derived from starch crosslinked with octenylsuccinate anhydride, sold under the name Dry-Flo by National Starch. Mixtures are possible.

The composition is preferably devoid of active principle unstable in an oxidizing environment at a content of 0.01 to 20% of the weight of the composition. A preferred example of such an unstable active principle is ascorbic acid.

Another preferred embodiment of the invention is a composition that includes, in a physiologically acceptable medium, an aqueous phase dispersed in an oily phase, characterized in that the oily phase contains particles of a crosslinked solid organopolysiloxane elastomer having at least one oxyalkylene group and in that the aqueous phase contains at least one crosslinked and neutralized poly(2-acrylamido-2-methylpropanesulphonic acid) polymer, the composition being devoid of active principle unstable in an oxidizing environment at a content of 0.01 to 20% of the total weight of the composition.

EXAMPLES

Having generally described this invention, a further understanding can be obtained by reference to certain specific examples which are provided herein for purposes of illustration only and are not intended to be limiting unless otherwise specified. The amounts are given therein as % by weight, unless otherwise mentioned.

Example 1

Body Cream

| A. Oily phase | |
|---|---|
| Cyclohexamethicone | 15% |
| Modified silicone (Example 3 of U.S. 5,412,004) | 8% |
| | (i.e. 2.64% of active material) |
| B. Aqueous phase | |
| Glycerol | 5% |
| Hostacerin AMPS | 1% |
| Water | 71% |

Procedure: the two phases are prepared separately and the gelled aqueous phase is introduced into the oily phase with stirring. A white cream is obtained which is very stable over time and which confers a strong feeling of freshness when applied to the skin.

Example 2

Face Cream

| A. Oily phase | |
|---|---|
| Cyclohexamethicone | 10% |
| Isohexadecane | 5% |
| Modified silicone (Example 3 of U.S. 5,412,004) | 3% |
| | (i.e. 0.99% of active material) |
| B. Aqueous phase | |
| Hostacerin AMPS | 1% |
| Preservative | 0.4% |
| Water | q.s. for 100 |

The procedure is the same as in Example 1. A smooth, soft, fresh and non-sticky emulsion is obtained which has a viscosity of approximately 38 DU (i.e. 90 poises 9 Pa·s) (measured at approximately 25° C. with a Mettler Rheomat viscometer, rotor 4).

Comparative Examples

The Hostacerin AMPS was replaced in Example 2 with gelling agents commonly used in cosmetic compositions, in an equivalent amount:

Carbopol (sold by Goodrich) is a carboxyvinyl polymer (CTFA name: carbomer).

Sepigel 305 (sold by Seppic) is an inverse emulsion of crosslinked copolymer obtained from acrylamide and from the sodium salt of 2-acrylamido-2-propanesulphonic acid, in a ratio as mol % of approximately 70/30 to 30/70 and preferably of 60/40 to 40/60, and from a polyfunctional monomer as crosslinking agent. This copolymer is more particularly disclosed in the document EP-A-503 853.

Pemulen (sold by Goodrich) is a copolymer of monoolefinically unsaturated $C_3$–$C_6$ carboxylic acid or acid anhydride and of acrylic acid ester comprising a fatty chain having from 10 to 30 carbon atoms (CTFA name: acrylates/C10–C30 alkyl acrylate crosspolymer).

The table shown below clearly displays the advantages of the composition according to the invention with respect to the compositions that contain, instead of the polymer used according to the invention, a gelling agent generally used in cosmetic compositions.

TABLE

| Composition | Example 2 according to the invention | Comparative Example 1 | Comparative Example 2 | Comparative Example 3 |
|---|---|---|---|---|
| Cyclohexa-methicone | 10% | 10% | 10% | 10% |
| Branched hydrocarbon | 5% | 5% | 5% | 5% |
| Modified silicone | 3% | 3% | 3% | 3% |
| Hostacerin AMPS | 1% | — | — | — |
| Sepigel 305 | — | 2.5% (i.e. 1% of active material) | — | — |
| Carbopol | — | — | 1% | — |
| Pemulen | — | — | — | 1% |
| Preservative | 0.4% | 0.4% | 0.4% | 0.4% |

TABLE-continued

| Composition | Example 2 according to the invention | Comparative Example 1 | Comparative Example 2 | Comparative Example 3 |
|---|---|---|---|---|
| Water | q.s. for 100% | q.s. for 100% | q.s. for 100% | q.s. for 100% |
| Viscosity at approx. 25° C. (Mettler Rheomat viscometer) | 90 poises (9 Pa · s) | 57 poises (5.7 Pa · s) | 52 poises (5.2 Pa · s) | Less than 5 poises (<5 Pa · s) |
| Macroscopic appearance | Smooth, soft, fresh and non-sticky emulsion, remains stable after 2 months at any temperature after freezing cycles | Fluid emulsion of oily appearance with release of oil. Phase separation after 15 days. | Fluid emulsion, sticky and clingy feel, with a rough effect. Phase separation after freezing cycles. | Very fluid emulsion with a heterogeneous appearance, not smooth but granular with a sticky feel. Phase separation after freezing cycles. |
| Appearance under the microscope | Even emulsion with sharp edges | Uneven and coarse emulsion with wide release ranges | Coarse dispersion, rapidly destabilized with separation of the phases | Heterogeneous dispersion |

Example 3

Moisturizing Cream

A. Oily phase

| | |
|---|---|
| Cyclomethicone | 10% |
| Branched hydrocarbon | 5% |
| Modified silicone (Example 3 of U.S. 5,412,004) | 5% |
| | (i.e. 1.65 of active material) |

B. Aqueous phase

| | |
|---|---|
| Hostacerin AMPS | 1% |
| Glycerol | 7% |
| Preservative | 0.4% |
| Water | q.s. for 100 |

The procedure is the same as in Example 1. A smooth, soft, fresh and non-sticky emulsion is obtained.

Example 4

Make-Up Remover for Dry and Sensitive Skin

A. Oily phase

| | |
|---|---|
| Cyclopentamethicone | 10% |
| Mineral oil | 5% |
| Isopropyl palmitate | 10% |
| Modified silicone (Example 3 of U.S. 5,412,004) | 10% |
| | (i.e. 3.3% of active material) |

B. Aqueous phase

| | |
|---|---|
| Hostacerin AMPS | 0.5% |
| Glycerol | 3% |
| Preservative | 0.4% |
| Water | q.s. for 100% |

The procedure is the same as in Example 1. A supple, soft and fresh emulsion which is easy to spread is obtained. This emulsion has good make-up-removing properties and leaves the skin clean, fresh and matt.

Example 5

Mattifying Foundation

A. Oily phase

| | |
|---|---|
| Cyclohexamethicone | 10% |
| Branched hydrocarbon | 5% |
| Isopropyl palmitate | 10% |
| Modified silicone (Example 3 of U.S. 5,412,004) | 15% |
| | (i.e. 4.95% of active material) |

B. Phase of the fillers and pigments

| | |
|---|---|
| Red, brown and yellow pigments | 5% |
| Crosslinked starch (Dry-Flo from National Starch) | 5% |

C. Aqueous phase

| | |
|---|---|
| Hostecerin AMPS | 1% |
| Glycerol | 7% |
| Preservative | 0.4% |
| Water | q.s. for 100% |

Procedure: the aqueous and oily phases are prepared separately. The pigments and fillers are dispersed in the oily phase and the gelled aqueous phase is introduced into the oily phase with stirring. A soft foundation is obtained which is very pleasant to use and which gives a smooth and matt appearance to the skin.

Obviously, numerous modifications and variations of the present invention are possible in light of the above teachings. It is therefore to be understood that within the scope of the appended claims, the invention may be practiced otherwise than as specifically described herein.

This application is based on French patent application 0003589, filed Mar. 21, 2000, the entire contents of which are hereby incorporated by reference, the same as if set forth at length.

What is claimed is:

1. A water in oil emulsion, comprising:
   an aqueous phase dispersed in an oily phase;
   wherein said oily phase comprises at least one particle of a crosslinked solid organopolysiloxane elastomer having at least one oxyalkylene group,
   and wherein said aqueous phase comprises at least one crosslinked and at least partially neutralized poly(2-acrylamido-2-methylpropanesulphonic acid) polymer.

2. The water in oil emulsion according to claim 1, wherein said oxyalkylene group is an oxyethylene group.

3. The water in oil emulsion according to claim 1, wherein said organopolysiloxane elastomer comprises only an oxyethylene group or groups as said oxyalkylene group.

4. The water in oil emulsion according to claim 1, wherein said organopolysiloxane elastomer is obtained by an addition and crosslinking reaction in a non-aqueous medium, in the presence of a catalyst, of at least:
   one first organopolysiloxane (i) having at least two vinyl groups in the α,Ω-position of the silicone chain per molecule; and
   one second organopolysiloxane (ii) having at least one hydrogen atom bonded to a silicon atom per molecule and at least one oxyalkylene group.

5. The water in oil emulsion according to claim 4, wherein said first organopolysiloxane (i) comprises at least one polydimethylsiloxane.

6. The water in oil emulsion according to claim 4, wherein said first organopolysiloxane (i) is an α,Ω-dimethylvinylpolydimethylsiloxane.

7. The water in oil emulsion according to claim 4, wherein said second organopolysiloxane (ii) comprises at least one polydimethylsiloxane comprising:
   one or more hydrogen atoms, each bonded to a silicon atom, and
   one or more oxyalkylene groups bonded to a silicon atom via an alkylene radical having from 1 to 22 carbon atoms.

8. The water in oil emulsion according to claim 1, wherein said organopolysiloxane elastomer solid is in the form of a gel.

9. The water in oil emulsion according to claim 1, wherein said organopolysiloxane elastomer is in the form of a gel obtained according to the following stages:
   (a) mixing:
       at least one first organopolysiloxane (i) having at least two vinyl groups in the α,Ω-position of the silicone chain per molecule, with
       at least one second organopolysiloxane (ii) having at least one hydrogen atom bonded to a silicon atom per molecule and at least one oxyalkylene group, to obtain a mixture;
   (b) adding an oily phase to the mixture obtained in (a);
   (c) polymerizing the first and second organopolysiloxanes (i) and (ii) in the oily phase added in (b) in the presence of a platinum catalyst.

10. The water in oil emulsion according to claim 1, wherein organopolysiloxane elastomer solid is in the form of a gel, and wherein said gel has a dominant elastic nature at low values of the shear stress defined as follows: 800 Pa<$G^*_{plate}$<2,500 Pa with $\delta_{plate}$ in the region of 10°, $G^*_{plate}$ representing the consistency and $\delta_{plate}$ representing the elasticity, this measurement being made at 1 Hz.

11. The water in oil emulsion according to claim 1, wherein said organopolysiloxane elastomer particle has a size ranging from 3 to 200 μm.

12. The water in oil emulsion according to claim 1, wherein said organopolysiloxane elastomer particle has a size ranging from 3 to 50 μm.

13. The water in oil emulsion according claim 1, wherein said organopolysiloxane elastomer is present in an amount, as active material, ranging from 0.1 to 10% by weight with respect to the total weight of the water in oil emulsion.

14. The water in oil emulsion according to claim 1, wherein said poly(2-acrylamido-2-methylpropane sulphonic acid) comprises, distributed randomly:
   a) from 90 to 99.9 by weight of units of following formula (I):

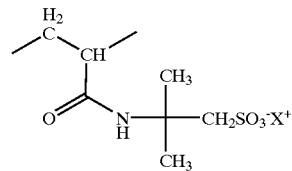

in which $X^+$ denotes a cation or a mixture of cations; and
   b) from 0.01 to 10% by weight of crosslinking units originating from at least one crosslinking monomer having at least two olefinic double bonds; the proportions by weight being defined with respect to the total weight of the crosslinked and neutralized poly(2-acrylamido-2-methylpropane sulphonic acid) polymer.

15. The water in oil emulsion according to claim 14, wherein in said formula (I), at most 10 mol % of said $X^+$ cations in said mixture of cations are $H^+$ protons.

16. The water in oil emulsion according to claim 14, wherein said poly(2-acrylamido-2-methylpropanesulphonic acid) comprises from 98 to 99.5 by weight of said units of formula (I) and from 0.2 to 2% by weight of said crosslinking units; the proportions by weight being defined with respect to the total weight of the crosslinked and neutralized poly(2-acrylamido-2-methylpropane sulphonic acid) polymer.

17. The water in oil emulsion according to claim 14, wherein in said formula (I), $X^+$ comprises $NH_4^+$.

18. The water in oil emulsion according to claim 14, wherein said crosslinking monomer corresponds to the following formula (II):

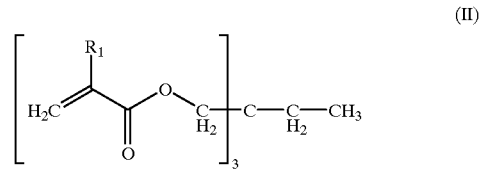

in which $R_1$ denotes hydrogen or a $C_1$–$C_4$ alkyl.

19. The water in oil emulsion according to claim 1, wherein said poly(2-acrylamido-2-methylpropanesulphonic acid) is crosslinked with trimethylolpropane triacrylate.

20. The water in oil emulsion according to claim 1, wherein said poly(2-acrylamido-2-methylpropanesulphonic acid) is present in an amount ranging from 0.1 to 10% by weight of active material with respect to the total weight of the oil in water emulsion.

21. The water in oil emulsion according to claim 1, wherein said oily phase is present in an amount ranging from 5 to 50% by weight with respect to the total weight of the oil in water emulsion.

22. The water in oil emulsion according to claim 1, wherein said oily phase comprises at least one volatile silicone oil.

23. The water in oil emulsion according to claim 1, wherein said aqueous phase represents at least 65% by weight with respect to the total weight of the water in oil emulsion.

24. The water in oil emulsion according to claim 1, which does not contain any electrolyte.

25. The water in oil emulsion according to claim 1, which does not contain any active principle that is unstable in an oxidizing environment at a content of 0.01 to 20% of the total weight of the water in oil emulsion.

26. A method of using the water in oil emulsion according to claim 1, comprising applying said water in oil emulsion to at least one selected from the group consisting of hair, scalp, skin, lips, nails, mucous membranes and combinations thereof.

27. The method according to claim 26, further comprising at least one selected from the group consisting of treating, protecting, caring for, removing make-up from, or cleansing the skin, scalp, lips, hair, nails, mucous membranes and combinations thereof.

28. The method according to claim 26, further comprising making up the skin and/or lips.

29. A method of treating greasy skin, hair, lips or scalp, comprising applying the water in oil emulsion according to claim 1 to at least one selected from the group consisting of skin, hair, lips, scalp and combinations thereof.

30. A cosmetic or dermatological composition, comprising the water in oil emulsion according to claim 1 and a pharmaceutically acceptable medium.

31. The cosmetic or dermatological composition according to claim 30, which is in the form of a cream.

32. The cosmetic or dermatological composition according to claim 30, which is in the form of a greasy skin treatment composition.

33. A method for stabilizing a water-in-oil emulsion comprising an aqueous phase dispersed in an oily phase, said method comprising:

contacting said oily phase with at least one particle of a crosslinked solid organopolysiloxane elastomer having at least one oxyalkylene group; and contacting said aqueous phase with at least one crosslinked and at least partially neutralized poly(2-acrylamido-2-methylpropanesulphonic acid) polymer, to stabilize said water-in-oil emulsion.

34. A method of preparing a water-in-oil emulsion, comprising:

dispersing an aqueous phase in an oily phase; wherein said oily phase comprises at least one particle of a crosslinked solid organopolysiloxane elastomer having at least one oxyalkylene group; and said aqueous phase comprises at least one crosslinked and partially neutralized poly(2-acrylamido-2-methylpropanesulphonic acid) polymer.

* * * * *

UNITED STATES PATENT AND TRADEMARK OFFICE
CERTIFICATE OF CORRECTION

PATENT NO. : 6,509,024 B2
DATED : January 21, 2003
INVENTOR(S) : Raluca Lorant

It is certified that error appears in the above-identified patent and that said Letters Patent is hereby corrected as shown below:

Column 15,
Lines 19, 27 and 45, "Ω" should read -- ω --.

Column 16,
Line 57, "oil in water" should read -- water in oil --. (second occurrence)

Signed and Sealed this

Tenth Day of June, 2003

JAMES E. ROGAN
*Director of the United States Patent and Trademark Office*